(12) United States Patent
Keep et al.

(10) Patent No.: US 7,421,894 B2
(45) Date of Patent: Sep. 9, 2008

(54) SENSORS AND ASSOCIATED METHODS, INCLUDING SURFACE CONDITION SENSORS

(76) Inventors: Dale Keep, 2151 Granite Dr., Walla Walla, WA (US) 99362; Lance Doyle, 1887 W. Hwy. 12, Walla Walla, WA (US) 99362

( * ) Notice: Subject to any disclaimer, the term of this patent is extended or adjusted under 35 U.S.C. 154(b) by 0 days.

(21) Appl. No.: 11/506,646

(22) Filed: Aug. 18, 2006

(65) Prior Publication Data

US 2007/0163339 A1 Jul. 19, 2007

Related U.S. Application Data

(63) Continuation-in-part of application No. 11/487,157, filed on Jul. 13, 2006.

(60) Provisional application No. 60/699,931, filed on Jul. 14, 2005.

(51) Int. Cl.
*G01W 1/00* (2006.01)

(52) U.S. Cl. .................................. 73/170.19; 73/432.1

(58) Field of Classification Search .................... 73/146, 73/170.19; 340/905, 585
See application file for complete search history.

(56) References Cited

U.S. PATENT DOCUMENTS

| 3,891,979 | A * | 6/1975 | Braun et al. ................ 340/581 |
| 4,926,163 | A * | 5/1990 | Beebe ......................... 340/581 |
| 5,745,051 | A * | 4/1998 | Doherty et al. ............. 340/905 |
| 6,300,865 | B1 * | 10/2001 | Fechner et al. .............. 340/436 |
| 6,441,748 | B1 * | 8/2002 | Takagi et al. ................ 340/901 |
| 6,662,099 | B2 * | 12/2003 | Knaian et al. ............... 701/117 |
| 6,977,597 | B2 * | 12/2005 | Doherty ...................... 340/905 |
| 7,164,365 | B2 * | 1/2007 | Doherty et al. ............. 340/905 |
| 2002/0177942 | A1 * | 11/2002 | Knaian et al. ............... 701/117 |
| 2003/0178501 | A1 * | 9/2003 | Doherty ........................ 239/1 |
| 2005/0206526 | A1 * | 9/2005 | Ozawa et al. ............... 340/580 |

* cited by examiner

*Primary Examiner*—Andre J Allen

(57) ABSTRACT

An embodiment of the present invention provides a surface sensor system comprising a wet/dry sensor assembly, an electrically isolated passive sensor assembly, a thermally adjustable active sensor assembly, at least one temperature sensor, and a data processing device coupled together as a unit positionable adjacent to a surface, such as an outdoor surface. The unit is configured to determine the presence a surface material containing water or a water-based mixture on the surface and the solid or liquid phase of the surface material.

8 Claims, 5 Drawing Sheets

SENSORS AND ASSOCIATED METHODS, INCLUDING SURFACE CONDITION SENSORS

CROSS REFERENCE TO RELATED APPLICATIONS

This patent application is a continuation in part of U.S. patent application Ser. No. 11/487,157, filed Jul. 13, 2006, entitled SENSORS AND ASSOCIATED METHODS, INCLUDING SURFACE CONDITION SENSORS, which claimed the benefit of U.S. Provisional Patent Application No. 60/699,931, entitled "ROADWAY SENSOR SYSTEM", filed Jul. 14, 2005, both of which are incorporated herein in there entirety by reference thereto.

TECHNICAL FIELD

The following disclosure relates generally to sensors and associated methods, including surface condition sensors.

BACKGROUND

Surface conditions of a road or runway can change rapidly with changes in weather and other environmental conditions. These changes in surface and weather conditions can greatly affect the operation of vehicles operating on these surfaces. If the surface conditions are known, the vehicle operator can take these conditions into consideration when operating the vehicle. For example, the vehicle operator may reduce speed and increase following distances when driving on a wet road. Additionally, when surface conditions are known, maintenance crews may be able to take actions to improve the conditions. Accordingly, it can be important to track changes in conditions associated with roads, runways, and the like in a timely manner. This information can then be provided to a variety of users including maintenance crews and vehicle operators.

SUMMARY

The present invention provides a sensor system, such as a sensor system for sensing conditions on a surface. In one embodiment the sensor system comprises a wet/dry sensor assembly, an electrically isolated passive sensor assembly, a thermally adjustable active sensor assembly, at least one temperature sensor, and a data processing device coupled together as a unit positionable adjacent to the surface. The unit is configured to determine the presence a surface material containing water or a water-based mixture on the surface and the solid or liquid phase of the surface material.

Another embodiment of a surface sensor system comprises an electrically isolated passive sensor assembly having first and second electrodes spaced apart from each other and interconnected by an electrically conductive member. The electrically conductive member is positioned adjacent to at least one winding. A detection device is connected to the winding and is configured to detect and measure an electrical condition in the electrically conductive member as a function of electrical conductivity of material on the surface. The detection device is in electrical contact with the first and second electrodes.

Another embodiment of a surface sensor system comprises an active sensor assembly configured to determine the presence a surface material containing water or a water-based mixture on a surface, such as an outdoor surface, and the solid or liquid phase of the surface material. The active sensor assembly has a temperature sensor, first and second electrodes spaced apart from each other, and a temperature adjustment device thermally connected to the first and second electrodes. The thermal adjustment device is configured to heat or cool at least one of the first and second electrodes to change at least one of the temperature and the phase of the surface material.

Yet another embodiment of a surface sensor system comprises an electrically insulative body having a surface portion positionable substantially coplanar with the surface. A data processing system is positioned within the body. A first sensor assembly is coupled to the data processing system and has a first temperature sensor and a conductivity sensor unit within the body and coupled to the surface portion. The conductivity sensor unit has a plurality of sensing electrodes coupled to the surface portion and electrically isolated from each other by a plurality of non-conductive layers interleaved between the sensing electrodes. The conductivity sensor unit is configured to detect if the surface portion is wet, partially wet, or dry.

A second sensor assembly is positioned within the body and spaced apart from the first sensor assembly. The second sensor assembly is coupled to the data processing system. The second sensor assembly has first and second electrodes spaced apart from each other and interconnected by an electrically conductive member. At least a portion of the first and second electrodes are substantially coplanar with the surface portion. The electrically conductive member is positioned adjacent to first and second windings spaced apart from each other. A detection device is connected to the first and second windings and is configured to detect and measure an electrical condition in the electrically conductive member based upon the conductivity of material on the surface portion and in contact with the first and second electrodes.

DETAILED DESCRIPTION

The present invention describes sensors and associated methods, including surface condition sensors. Several specific embodiments are set forth in the following description and in FIGS. 1-6 to provide a thorough understanding of certain embodiments of the invention. One skilled in the art, however, will understand that the present invention may be practiced without several of the specific features explained in the following description.

Certain embodiments of the invention includes a device used to determine weather-related surface conditions, such as the surface condition on a highway, a runway, parking lot, and/or other outdoor surfaces. For example, a sensor system (e.g., a surface sensor system and/or an intelligent sensor) can be encapsulated in an electrically insulating body, support structure, encapsulant, or the like. In other embodiments, the sensor system can be used with other surfaces (e.g., an indoor ice rink to determine surface related conditions). The sensing system can include one or more sensor assemblies and can be used to sense or determine various surface conditions including, but not limited to, a presence of water, a presence of an anti-icing chemical, a presence of ice, a freeze point of a liquid (if any), a surface temperature, a pavement/ground temperature, and/or the like. The sensor system can also include devices, systems, or assemblies that allow the sensor to communicate directly to an end user, an operator, an intermediate data logging computer, a Remote Processing Unit (RPU), a Central Processing Unit (CPU), and/or other devices or systems.

Figure 1:
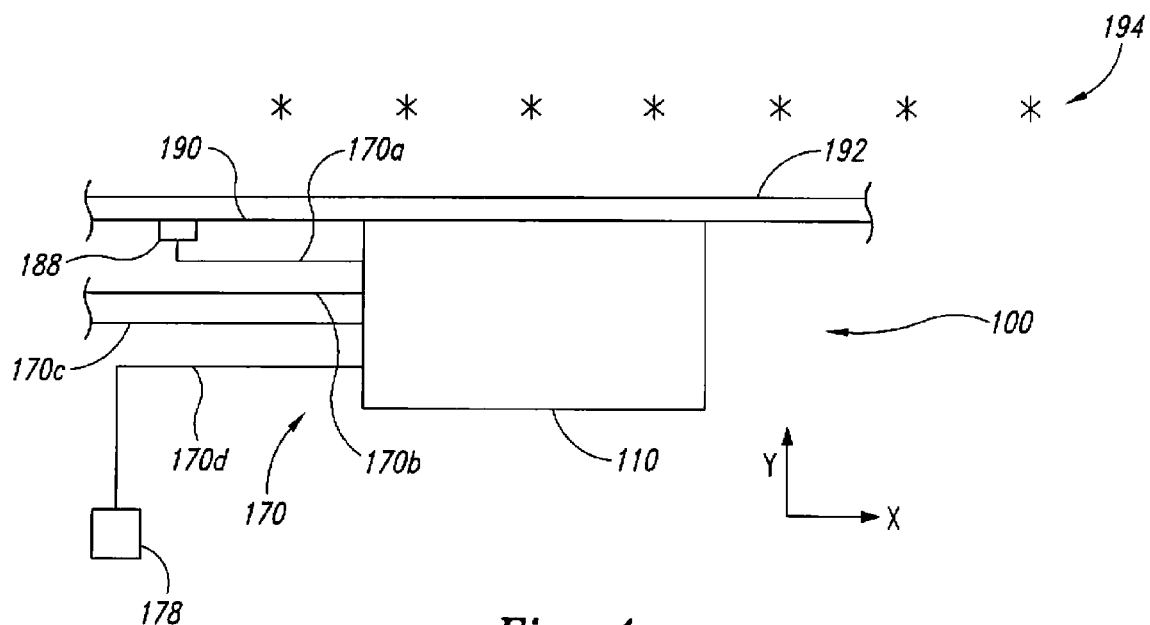
FIG. 1 is a partially schematic side elevation of a sensor system and a surface in accordance with certain embodiments of the invention.
Figure 2:
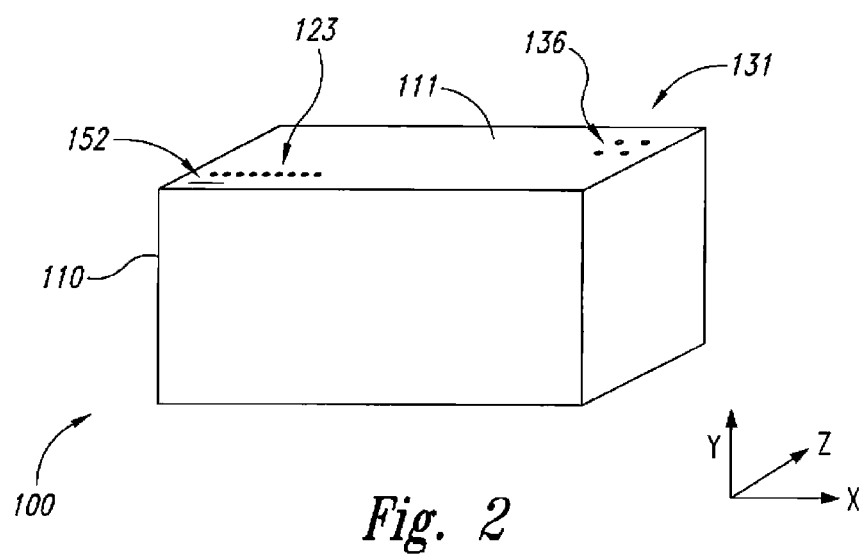
FIG. 2 is an isometric illustration of the sensor system shown in FIG. 1.

For example, FIG. 1 is a partially schematic side elevation of a sensor system 100 and a surface 190 in accordance with certain embodiments of the invention. FIG. 2 is an isometric illustration of the sensor system 100 shown in FIG. 1. As shown in FIG. 2, the sensing system 100 includes a body 110, encapsulant, support structure, or the like forming an exterior of at least a portion of the sensing system 100. In selected embodiments, the body 110 can include an electrically insulating material and/or can at least approximately seal an internal potion of the sensing system 100 to protect various electronic components from liquid and debris.

In the illustrated embodiment, the sensing system 100 includes multiple sensor assemblies, including a temperature sensor assembly, a wet/dry sensor assembly, a passive sensor assembly, and an active sensor assembly. In other embodiments, the sensor system 100 can include more, fewer, and/or different sensor assemblies. Additionally, as discussed below in further detail, in the illustrated embodiment the various sensor assemblies can share various components. In other embodiments, each sensor assembly can have separate components.

In FIG. 2, a portion of a temperature sensor 152 associated with the temperature sensor assembly is shown on or proximate to the surface portion 111 (e.g., coupled to the surface portion 111), along with portions of sensing electrodes 123 associated with the wet/dry sensor assembly. Additionally, portions of conductivity electrodes 131 associated with both the passive and active sensor assemblies are shown on or proximate to the surface portion 111, along with portions of sensing electrodes 136 associated with the active sensing system. As shown in FIG. 1, the sensor system 100 can be positioned, embedded, and/or buried so that the surface portion 111 of the sensor system 100, along with the portions of sensors/electrodes discussed above are proximate to or substantially coplanar with the surface 190.

In FIG. 1, weather-related conditions 194 (e.g., precipitation) has caused surface material 192 to accumulate on or to be applied to at least a portion of the surface 190. As discussed in greater detail below, in selected embodiments the sensor system 100 can detect various parameters associated with the condition of the surface 190 and/or the material on the surface using the sensor assemblies discussed above. The parameters or information associated with these parameters can then be communicated to a user, operator, or other systems.

For example, in the illustrated embodiment the sensor system 100 includes one or more connectors 170 that can be used to exchange data or information with other local or remote devices, sensors, systems, or entities. Additionally, in certain embodiments these connectors can be used to transfer power. The connectors 170 can include multiple portions. For example, the portions of the connectors 170 shown in FIG. 1 include cables that enter the body 110 of the sensor system 100. In the illustrated embodiment, the connectors include additional internal components (e.g., circuitry to connect the cables to various devices and/or printed circuit boards). Although in FIG. 1 the connectors 170 include cables, in other embodiments the connectors 170 can include wireless transmitters/receivers.

In the illustrated embodiment, a first connector 170a is coupled to a remote sensor 188. For example, in selected embodiments the first connector 170a can be operatively coupled to a remote humidity sensor and/or a remote temperature sensor. In certain embodiments, the remote sensor 188 can be located proximate to the surface 190, buried beneath the surface 190 (e.g., to sense ground temperature at a selected depth), or located above the surface 190 (e.g., to sense air temperature).

In FIG. 1, a second connector 170b is operatively coupled to another sensor system, similar to the sensor system 100 discussed above. For example, as discussed below in further detail, the sensor system 100 can be operatively coupled to other similar sensor systems in a master-slave arrangement. A third connector 170c is operatively coupled to a communication device. For example, the communication device can include a telephone modem, a wireless modem, a network router, or the like. The fourth connector 170d is operatively coupled to a power supply 178, to provide power to the sensor system components.

Figure 3:
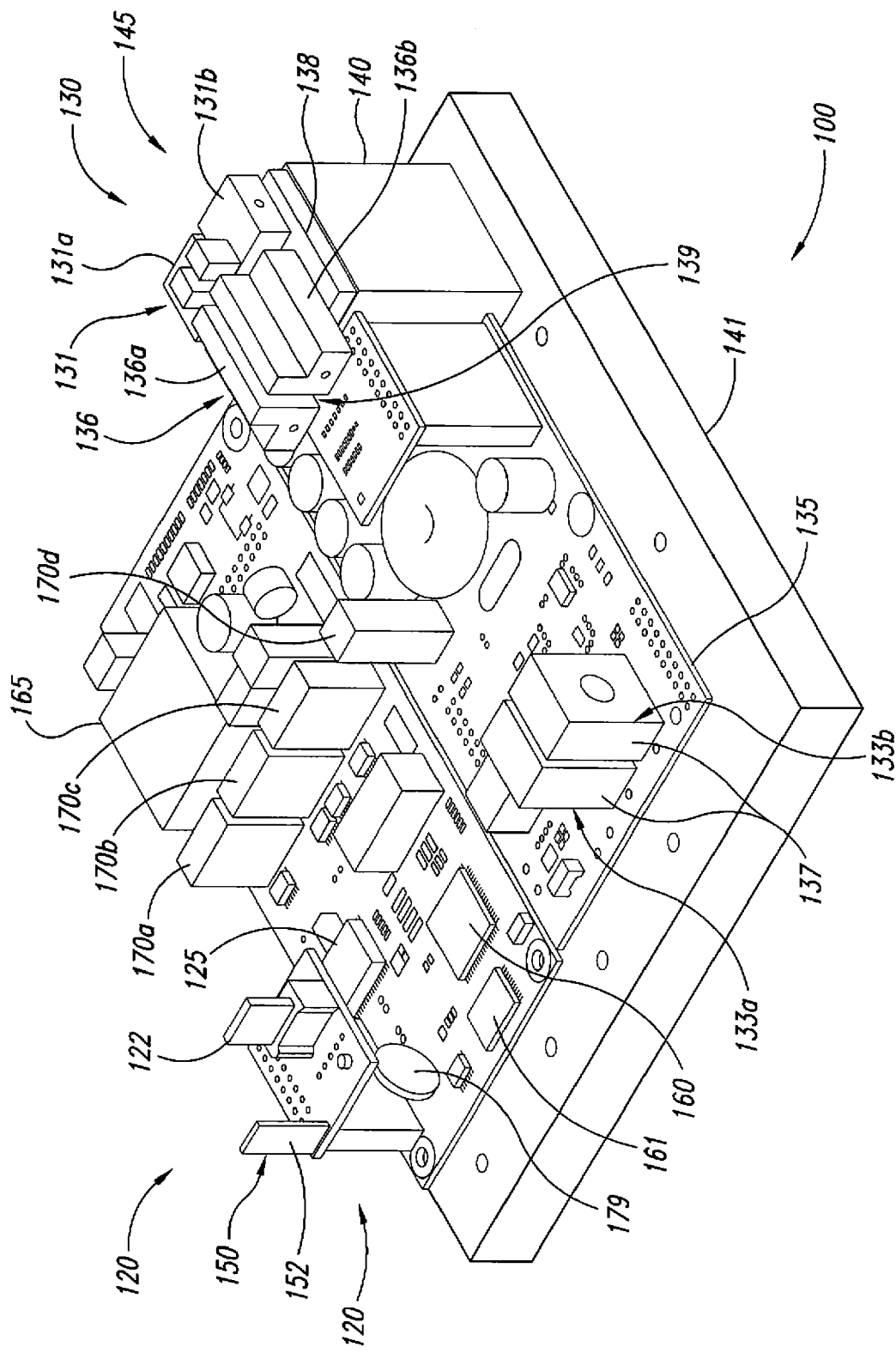
FIG. 3 is an isometric illustration of a portion of the sensor system shown in FIG. 1.

FIG. 3 is an isometric illustration of a portion of the sensor system 100 shown in FIG. 1. FIG. 3 illustrates various components associated with the sensor system 100, including components associated with each of the sensor assemblies discussed above. Accordingly, the sensor system 100 and each of the sensor assemblies will be discussed below in further detail with reference to FIG. 3.

In FIG. 3, the sensor system 100 includes a data processing system or data processing device 160 (e.g., a computing system). The data processing device 160 can perform various functions, including controlling the operation of various sensor components, processing data collected by the various sensor assemblies, providing/coordinating communication internal and external to the sensor system body 110, controlling power connection/distribution, and the like. The data processing device 160 can be a single unit operatively coupled to various components or can be distributed throughout various components within the sensor system body 110 and/or exterior to the sensor system body 110. The data processing device 160 can also include various memory and or data storage device. For example, in FIG. 3 the data processing device 160 includes a memory device 161.

In the illustrated embodiment, the internal portions of the connectors 170 are shown. For example, the first connector 170a provides communication between the data processing device 160 and the remote sensor 188 (shown in FIG. 1) via a printed circuit board. The second connector 170b provides communication between the data processing device 160 and other sensor systems similar to the illustrated sensor system 100 via a printed circuit board. The third connector 170c provides communication between the data processing device 160 and other devices, other systems, users, operators, and the like via a printed circuit board and a communication device 165. The fourth connector 170d provides power (e.g., electrical power) to various sensor system components via a printed circuit board. The connectors 170 can be connected to the same printed circuit board or to different printed circuit boards coupled together (e.g., that support other circuitry and/or components of the sensor system). Self-contained back-up power source 179 can provide power to some or all of the sensor system 100 for a selected period of time in the event that the power being received via the fourth connector 170d fails. For example, in selected embodiments the self-contained back-up power source 179 can provide power to the data processing unit 160 in the event of a power failure.

In FIG. 3, the temperature assembly 150 includes the temperature sensor 152 coupled to a printed circuit board. The printed circuit board can contain circuitry that allows the temperature sensor to communicate with other portions of the sensor system 100. In the illustrated embodiment, a portion of the temperature sensor is positioned so that it is at least approximately or substantially coplanar with the surface portion 111 of the sensor system body 110 (shown in FIG. 2) and so that it can detect temperature at the surface portion and/or the surface 190 (shown in FIG. 1). In certain embodiments, the temperature sensor can include a shielding element that physically protects the portion of the temperature sensor proximate to the surface 190. In selected embodiments, the temperature sensor assembly can share data with various other sensor assemblies. In other embodiments, each sensor assembly can include at least one dedicated temperature sensor. Accordingly, in other embodiments the sensor system 100 can include more temperature sensors and/or temperature sensor assemblies. Additionally, in still other embodiments the sensor system 100 can include temperature sensor assemblies/temperature sensors that have other configurations. For example, in selected embodiments the temperature sensor assembly and/or the temperature sensor can be located externally and apart from the sensor system body 110.

Figure 4:
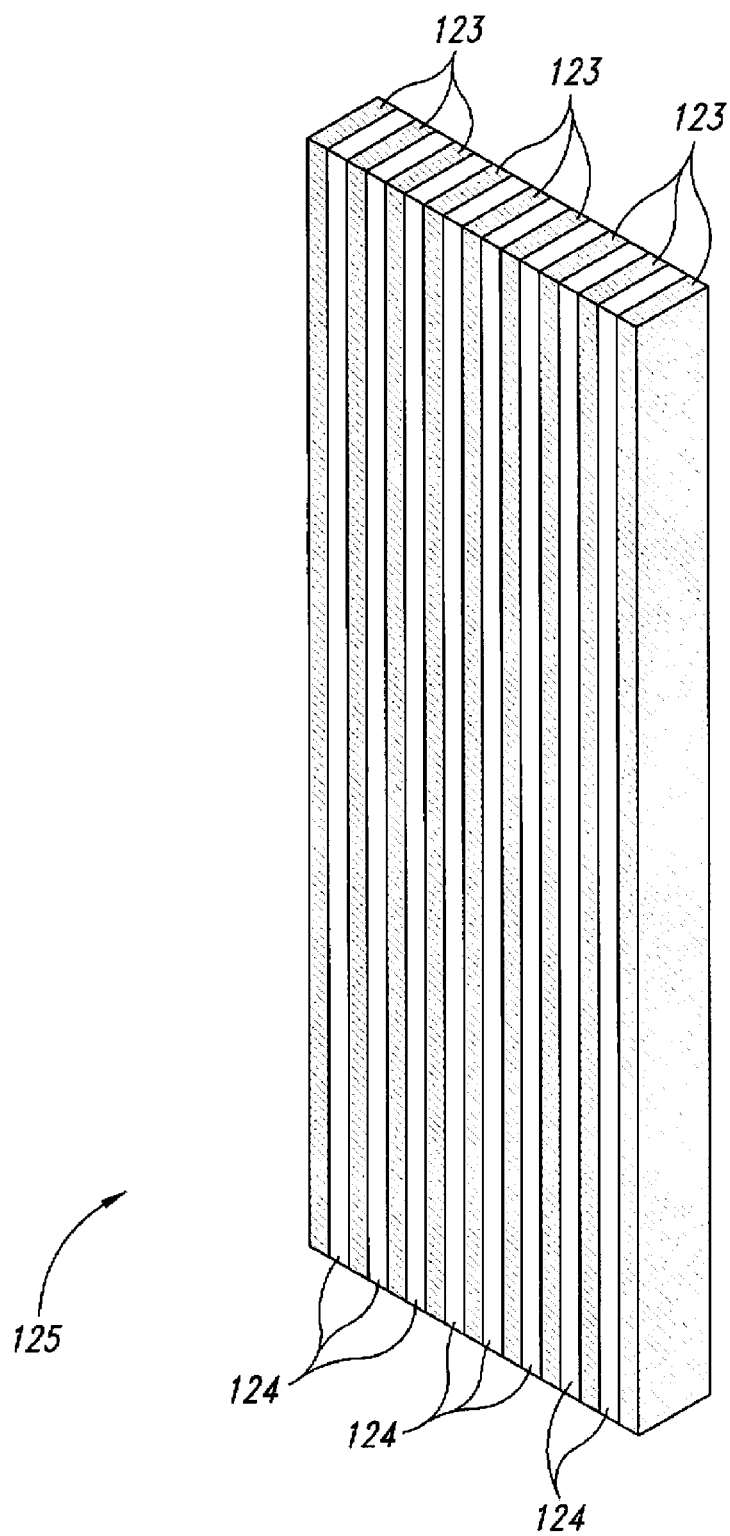
FIG. 4 is an isometric illustration of an electrode assembly of the sensor system shown in FIG. 1.

As discussed above, the sensor system 100 in the illustrated embodiment includes a wet/dry sensor assembly 120. In the illustrated embodiment, the wet/dry sensor assembly 120 includes a controller 125 and an electrode assembly 122. The electrode assembly is operatively coupled to the controller 125 and to the data processing device 160 via one or more printed circuit boards. As shown in FIG. 4, the electrode assembly 125 includes a plurality of sensing electrodes 123 electrically isolated from each other by a plurality of electrically insulative layers 124 interleaved between the sensing electrodes. The controller is configured to control a sequence and timing of electrical stimulation of each of the sensing electrodes to detect the wet/dry status of the surface/surface material. In the illustrated embodiment, the wet/dry sensor assembly 120 includes the temperature assembly 150, however, in other embodiments the wet/dry sensor can include a dedicated temperature sensor.

In the illustrated, the wet/dry sensor 120 can detect the presence of small amounts of moisture on a surface. Additionally, in certain embodiments the wet/dry sensor 120 can accurately report dry surfaces even in the presence of dry salt crystals (commonly used deicer product) where false wet readings are often reported with the use of conventional technology. In certain embodiments, the wet/dry sensor 120 can provide wet to dry transitions data, and current surface conditions at three or more different levels, including wet, dry, and trace.

Additionally, in selected embodiments the wet/dry sensor 120 can provide the ability to set and adjust thresholds to enable accurate reporting of the three surface conditions and transitions between them. For example, in some embodiments the thresholds can be set at installation and/or adjusted by an operator via commands exchanged through the communication device 165. In certain embodiments, the threshold adjustments can be made to provide the wet, dry, or trace information to accommodate the needs of a selected consumer and/or environment/location. In still other embodiments, the wet/dry sensor 120 can apply automatic temperature compensation to provide wet, trace, and dry, condition data (e.g., based on the adjusted thresholds).

In selected embodiments, the controller 125 can include a Freescale Semiconductor MC33794 Electric Field Imaging Device (e.g., an integrated circuit) to drive the sensing electrodes 123. For example, this arrangement can be used to measure effective conductivity of materials on the surface of the sensor. In certain embodiments, there is no attempt to convert the measured value to a standard measurement value. In the illustrated embodiment this circuitry drives nine electrodes 123 sequentially.

In the illustrated embodiment, the electrodes 123 include a lamination of polymer-impregnated graphite and the insulative layers 124 include methylmethacrylate. In selected embodiments, the electrodes can be laminated and cut to fit into an edge card connector. This can facilitate electrically connecting and mechanical locating the electrodes 123 in the sensor system 100. In selected embodiments, the electrodes 123 can be chemically resistant to common liquids and deicing compounds; physically tough to withstand the abuse that they might be subjected to on a highway, airport environment (e.g., runway, taxiways, and the like), or other surfaces; and/ or resistant to ultraviolet light.

In the illustrated embodiment, the controller 125 generates a low radio frequency sine wave with low harmonic content. The controller 125 applies the AC coupled sine wave onto one electrode at a time while the other eight electrodes are grounded. The conductivity between the electrodes (e.g., based on the surface material proximate to the electrodes) can affect the current flow between the driven electrode and the grounded electrode(s). The circuit monitors the driven electrode and delivers a rectified and filtered voltage level to an analog to digital converter (e.g., an 8-bit Analog to Digital Converter). The voltage level is stored and the next electrode in sequence is stimulated and measured until all electrodes have been measured. In certain embodiments, the values can be measured against a temperature compensated table to determine if the value for each electrode is representative of a dry surface, a surface with a trace of moisture, or a wet surface. In the illustrated embodiment, the lowest values from any four electrodes are used to determine the surface condition.

In certain embodiments, an absolute threshold value is not set for the Dry/Trace or Trace/Wet conditions as many variables can influence these values. For example, these values can be influenced by the length of cables used, the size of the wet/dry electrodes, the analog to digital converter circuit used, the materials used for the electrodes, and the like.

In one embodiment, the typical threshold values for Dry/ Trace are 30,000 at 20° C. and are 28,000 at 20° C. for Trace/Wet. The temperature coefficient is −100 counts per ° C. for both thresholds. The value of the temperature coefficient is linear and the slope is −100. As such, for each degree Celsius the temperature raises, a value of 100 is subtracted from the base threshold setting. For each degree Celsius the temperature drops, a value of 100 is added to the base threshold setting. The formula for this embodiment is:

$$Y = MX + B$$

Where
    Y equals the adjusted threshold value
    X equals the current surface Temperature
    B equals the threshold value at zero (0) degrees Celsius.

In selected embodiments, a state machine can be used to control the timing and sequencing of the electrode stimulation. Due to the time constant of the filter components and the input capacitance of the AD converter circuit, in certain embodiments the sequencer can remain or dwell at each electrode for a sufficient time to allow the voltage to settle.

As discussed above, the sensor system 100 in the illustrated embodiment also includes a passive sensor assembly 145. In FIG. 3, the passive sensor assembly 145 includes conductivity electrodes 131, shown as a first conductivity electrode 131a and a second conductivity electrode 131b. The first and second electrodes 131a and 131b are spaced apart from each other. The electrodes 131 are interconnected by an electrically conductive member (e.g., a wire) that passes through at least one winding assembly 133. For example, in the illustrated embodiment the electrodes 131 are electrically coupled to a printed circuit board, which in turn is coupled to the electrically conductive member that passes through a first winding assembly 133a and a second winding assembly 133b. In other embodiments, passive sensor assembly 145 can have other arrangements. For example, in selected embodiments the electrically conductive member can be connected or attached directly to the electrodes 131 or hardwired to the electrodes 131. In still other embodiments, the passive sensor assembly 145 can include more or fewer winding assemblies.

Figure 5:
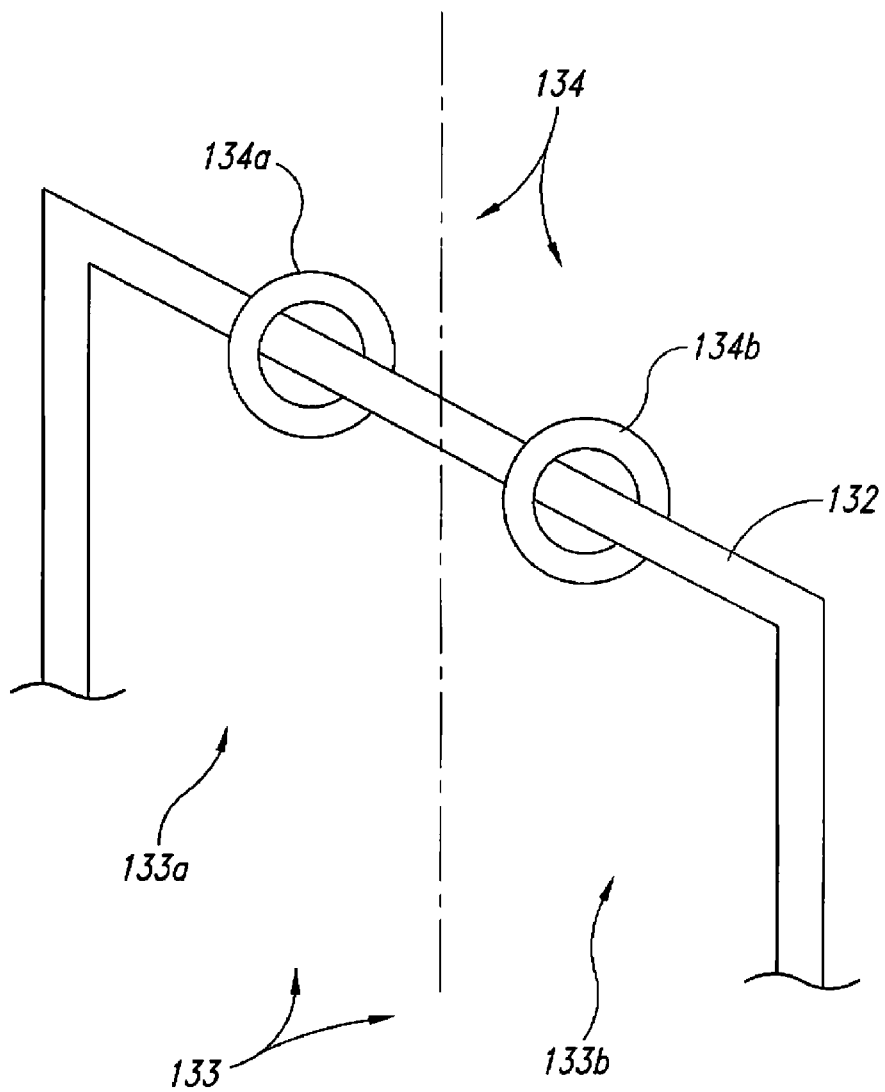
FIG. 5 is an isometric illustration of multiple windings of the sensor system shown in FIG. 1.

As shown in FIG. 5, each winding assembly 133 includes at least one winding 134 (e.g., a toroid shaped winding). For example, the first winding assembly 133a includes a first winding 134a and the second winding assembly 133b includes a second winding 134b. The electrically conductive member 132 is positioned adjacent to the first and second windings 134a and 134b. In the illustrated embodiment, each winding assembly 133 includes shielding material 137 proximate to the windings 134. For example, in selected embodiments shielding material 137 can partially or fully surround the windings 134 (e.g., shielding material can be positioned around 5 or 6 sides of the windings) and can be configured to block electromagnetic radiation.

Referring back to FIG. 3, a detection device 135 (e.g., the circuitry contained in/on a printed circuit board) is connected to the windings 134 (shown in FIG. 5) and configured to detect and measure an electrical condition in the electrically conductive member 132 (shown in FIG. 5) as a function of the electrical conductivity of material in electrical contact with the first and second electrodes. For example, the conductivity of the surface material on the surface 190 (shown in FIG. 1) and/or surface portion of the sensor system body 111 (shown in FIG. 2). In the illustrated embodiment, the detection device 135 is operatively coupled to the data processing device 160 via one or more printed circuit boards. In other embodiments, the passive sensor assembly can include other arrangements. For example, in other embodiments the windings 134 are electrically connected directly to the data processing device 160, and the data processing device provides the detection and measurement function of the associated electrical condition in the conductive member 132. Because in the illustrated embodiment, the electrodes are connected to the conductive member and the conductive member is physically isolated from the detection device, the electrodes are also physically isolated from the detection device.

In the illustrated embodiment, the first and second winding assemblies are mounted side by side on a multilayer Printed Circuit Board (PCB). One layer of the PCB is a ground plane. The windings are enclosed in a five sided magnetic and capacitive shield made of 0.004" thick CO-NETIC AA foil manufactured by Magnetic Shield Corporation. Each shield is connected to a pad on the Printed Circuit Board with a wire soldered to a via tied to the Ground plane. In selected embodiments, the shields (e.g., mumetal shields) can surround each winding and can reduce or limit capacitive coupling and/or magnetic coupling between the windings. In other embodiments, only one winding or a selected number of windings are surrounded by a shield.

In the illustrated embodiment, a crystal-controlled oscillator circuit is used to drive the windings. In certain embodiments, an operational amplifier can be used to provide the necessary gain to start and maintain oscillation. In the illustrated embodiment, an operational amplifier configured as a unity gain buffer is used to prevent loading of the oscillator circuit.

In the illustrated embodiment, the first electrode 131a is connected to the second electrode by a wire passing through the center of the windings. As discussed above, portions of the electrodes 131 are positioned flush or coplanar with the surface portion of the sensor and are exposed to whatever is present on the sensor's surface. When bare and dry, the surface portion can have an extremely high resistance. Accordingly, in the illustrated embodiment oscillating current in one winding will cause (e.g., induce) very little current to flow through the wire. Because little or no current flows through the wire, there will be little or no current induced in the second winding.

In FIG. 3, when moisture is present, the resistance on the surface portion can drop. When there is a conductive path with lower resistance between the electrodes 131, more current can flow through the wire. Accordingly, the current induced in the wire by the first winding will induce a current in the second winding (e.g., coupling energy from the first winding to the second winding). In certain cases, a resistance drop can be caused or influenced by the amount and type of impurities present and/or the amount of moisture. In some cases, when moisture freezes, the resistance can change (e.g., increase) as compared to the resistance associated with liquid moisture. For example, in certain cases water has a higher conductivity than ice, and thus, in selected embodiments the passive sensor assembly can also be used to indicate the formation of ice.

In selected embodiments an analog to digital converter is used to convert the output of the conductive member and winding arrangement (e.g., the voltage output of the second winding) to a digital signal before the output is sent to the data processing device 160. In selected embodiments, the data processing device uses the indication of conductivity from the passive sensor assembly 145 and the temperature from the temperature assembly 150 to determine a concentration of liquid on the surface and/or surface portion of the sensor system body. In other embodiments, the passive sensor assembly 145 includes the temperature sensor assembly 150 and/or includes a dedicated temperature sensor.

In selected embodiments, the passive sensor assembly can provide a rugged durable method for determining the conductivity of moisture present on a surface of the electrodes. In some embodiments, the conductivity of liquid on the surface of the electrodes can be used to determine the presence or non-presence of anti-icing chemicals and the concentration of these chemicals if they are present (e.g., because at least some of these chemicals can change the conductivity of the liquid as compared to water). In certain embodiments, depending on the concentration of anti-icing chemicals, the sensor system 100 (e.g., the data processing device 160) can utilize a database or look-up tables to determine the freeze point of the moisture/liquid on the surface.

In certain embodiments, the passive sensor assembly 145 can be at least partially electrically isolated by the electrically insulated material of the sensor system body (shown in FIG. 2) and by the use of the conductive member and winding arrangement. For example, in selected embodiments galvanic corrosion and/or plating of the electrodes can be avoided because there is no DC current at the electrodes. In some cases, corrosion and/or plating of the electrodes can cause data accuracy to deteriorate and can eventually cause the passive sensor to quit working all together.

As discussed above, the sensor system 100 in the illustrated embodiment also includes an active sensor assembly 130 (e.g., a thermally adjustable active sensor assembly). In FIG. 3, the active sensor assembly 130 includes sensing electrodes 136, shown as a first sensing electrode 136a and a second sensing electrode 136b. In other embodiments, the active sensor assembly 130 can include more or fewer sensing electrodes 136.

In the illustrated embodiment, the first and second electrodes 136a and 136b are spaced apart from each other. In FIG. 3, the active sensor assembly 130 also includes a temperature adjustment device 138 thermally connected or coupled to the first and second electrodes 136a and 136b. In the illustrated embodiment, the thermal adjustment device is configured to heat or cool at least one of the first and second electrodes 136a and 136b to change the temperature of the electrodes 136 and/or the phase or state of the surface material (shown in FIG. 1). For example, in selected embodiments the thermal adjustment device is configured to change the phase of the surface material proximate to the electrodes 136 from a liquid to a solid (e.g., ice) by changing the temperature.

In FIG. 3, the active sensor assembly 130 also includes all of the elements of the passive sensor assembly 145. As discussed above, the passive sensor system 145 included conductivity electrodes 131 for sensing the conductivity between the conductivity electrodes 131 based on the ambient surface condition proximate to the conductivity electrodes 131. As shown in FIG. 3, in the illustrated embodiment the conductivity electrodes 131 are also thermally connected or coupled to the thermal adjustment device 138 (e.g., a Peltier device, a device that can heat and/or cool the electrodes, or the like). Accordingly, in the illustrated embodiment, when the active sensor assembly 130 is in use, the thermal adjustment device 138 is configured to change the temperature (e.g., to a selected temperature) of the conductivity electrodes 131 and/or phase (e.g., to a selected phase) of the surface material proximate to the conductivity electrodes 131. Therefore, the components of the passive sensor assembly 145 can sense the conductivity of material proximate to, or on, the conductivity electrodes 131 at the selected temperature and/or selected phase.

The sensing electrodes 136 in FIG. 3 function similar to the sensing electrodes discussed above with reference to the wet/dry sensor assembly 120 and are used to determine a transition between surface conditions (e.g., wet, dry, and/or the like). In the illustrated embodiment, the same controller 125 associated with the wet/dry sensor assembly 120 is used to drive the sensing electrodes 136 of the active sensor assembly 130 in a sequential manner similar to the way the sensing electrodes 123 of the wet/dry sensor assembly 120 are driven. Data is gathered in a similar manner, except that the present embodiment of the active sensor assembly 130 only includes two sensing electrodes 136. In other embodiments, the active sensor assembly can have more or fewer sensing electrodes 136. In still other embodiments, the active sensor assembly 130 includes a dedicated controller to stimulate/run the sensing electrodes 136.

In the illustrated embodiment, the active sensor assembly 130 also includes a temperature sensor 139 for sensing the temperature of the thermal adjustment device 138 and/or any the electrodes 131 and 136 associated with the thermal adjustment device 138. Additionally, in FIG. 3 the active sensor assembly 130 includes at least one heat sink to improve the thermal control/response of the thermal adjustment device, electrodes 131 and 136, and surrounding areas, and/or to help protect sensor system electronics. In the illustrated embodiment, the active sensor assembly includes two heat sinks, shown as a first heat sink 140 and a second heat sink 141. In FIG. 3, the second heat sink includes at least a portion of the base of the sensor system 100. For example, at least a portion of a thermally conductive base.

In other embodiments, the active sensor assembly 130 can have other arrangements. For example, in other embodiments the active sensor assembly 130 includes more, fewer, or different electrodes/electrodes sets. For example, in selected embodiments the active sensor assembly include only one set of electrodes (e.g., either the sensing electrodes 136 or the conductivity electrodes 131). In other embodiments, the active sensor assembly 130 does not share components with other sensor assemblies and includes independent sensing electrodes 136 and conductivity electrodes 131, along with an independent associated conductive member and winding arrangement. In still other embodiments, the active sensor assembly 130 includes an independent temperature sensor for sensing the temperature of the surface material and/or the surface.

In various embodiments, data from various components of the active sensor assembly can be used and/or combined with data from other sensor assemblies to provided data to the data processing system for determining weather-related conditions of the material on the surface (shown in FIG. 1). For example, in certain embodiments, when determining a freeze point for material, the composition of the moisture (e.g., the amount of anti-icing chemicals present) doesn't matter when using the active sensor assembly because the actual freeze point of the surface material proximate to the electrodes can be determined by the temperature at which the surface material freezes. In other embodiments the active sensor assembly 130 can modify the temperature of a portion of surface material proximate to the electrodes in an attempt to freeze any moisture present and/or melt any ice present. In other cases, by cooling the moisture present on the surface and detecting when it freezes the freeze point of the moisture can be determined. Alternatively, heat can be applied to existing ice to determine that the ice melts or changes to water. In selected embodiments, when the presence of chemical(s) in the moisture or ice is known, the conductivity electrodes can be used to determine the concentration of chemical(s) present by the conductivity reading.

In one embodiment, an active freeze point determination process can include performing a "Cool Cycle" and/or a "Heat Cycle." In selected embodiments, a "Cool Cycle" can be performed by applying current in the correct direction to a Peltier device (e.g., a thermal adjustment device) to lower the temperature of the electrodes while monitoring the rate of change of conductivity ($\Delta c$) and the change of temperature ($\Delta t$). The data processing device can perform post processing on the collected data to examine the change in $\Delta c/\Delta t$. For example, if the slope of the $\Delta c/\Delta t$ changes significantly during the cool cycle, the temperature at which the slope changes can be the freeze point. In some cases, an empirically derived temperature offset can be applied to the freeze point to generate the actual freeze point of the solution on the surface of the sensor. This offset can be affected by the physical construction of the sensor and the specific materials used in the construction of the sensor. Additionally, in selected embodiments the sensing electrodes 136 data can be monitored during the "Cool Cycle." If the sensing electrodes 136 data indicate that the surface has changed from "Wet" to "Dry", then ice may have formed as ice can have a value similar to that of a dry surface.

In certain embodiments a "Heat Cycle" can be performed by applying current at reduced duty cycles in the correct direction to the Peltier device to increase the temperature of the electrodes while monitoring the rate of change of conductivity ($\Delta c$) and the change of temperature ($\Delta t$). For instance, the duty cycle of the power applied to the Peltier device can be varied to maintain an essentially constant rate of change of temperature during the "Heat Cycle". The parameters chosen are determined empirically based on the physical construction and the actual materials used in the construction of the sensor. The data processing device can perform post processing on the collected data to examine the change in $\Delta c/\Delta t$. For example, if the slope of the $\Delta c/\Delta t$ changes significantly during the "Heat Cycle", a "Melt" may have been detected. If a freeze point was detected during the "Cool Cycle" then the sensor may have made the ice. Otherwise, ice may have been present at the initiation of the "Active Cycle". If the Active Sensor's Wet/Dry electrodes detect changes from "Dry" to "Wet", this too can signify the presence of ice.

In selected embodiments, it can be determined whether the data is consistently linear by examining the data set. For example, assuming the data set consists of data points in the set P. For p∈P, p=(c,t) where c is conductivity reading and t is a temperature reading. For any two points $p_a$ and $p_b$ in P, the equation of a line that passes through them can be determined: c=st+i, where c is conductivity, s is slope, t is temperature and i is the intercept. By selecting multiple pairs of points, a set of linear functions F can be created. Each $f \in F$, $f=(s,i)$ where s is the slope, and i is the intercept of a linear function. It can be determined if the data set is consistently linear by comparing the slopes and intercepts of these functions.

In another embodiment, a hybrid active/passive freeze point can be determined as part of the heat cycle. For example, by determining the absolute value of the change in the conductivity readings relative to temperature, another freeze point value can be determined. In still another embodiment, a passive freeze point can be determined using the passive sensor assembly 145 (e.g., measuring ambient conditions without the heating or cooling of the thermal adjustment device). For example, in one embodiment conductivity values can be obtained at ambient conditions during using the passive sensor assembly 145. The ambient surface temperature can be collected using the temperature sensor assembly 150. Conductivity values can be normalized to 33.8° F. (1° C.) using empirically data. The normalized conductivity value can then be indexed to a lookup table to determine a passive freeze point. In selected embodiments, the data from the temperature sensor assembly, the active freeze point cycle, the hybrid active/passive freeze point, and the passive freeze point can be compared to determine a sensor system reported and/or predicted freeze point. In other embodiments, other data and/or combinations of the freeze points discussed above can be used to determine a sensor system reported and/or predicted freeze point.

Figure 6:
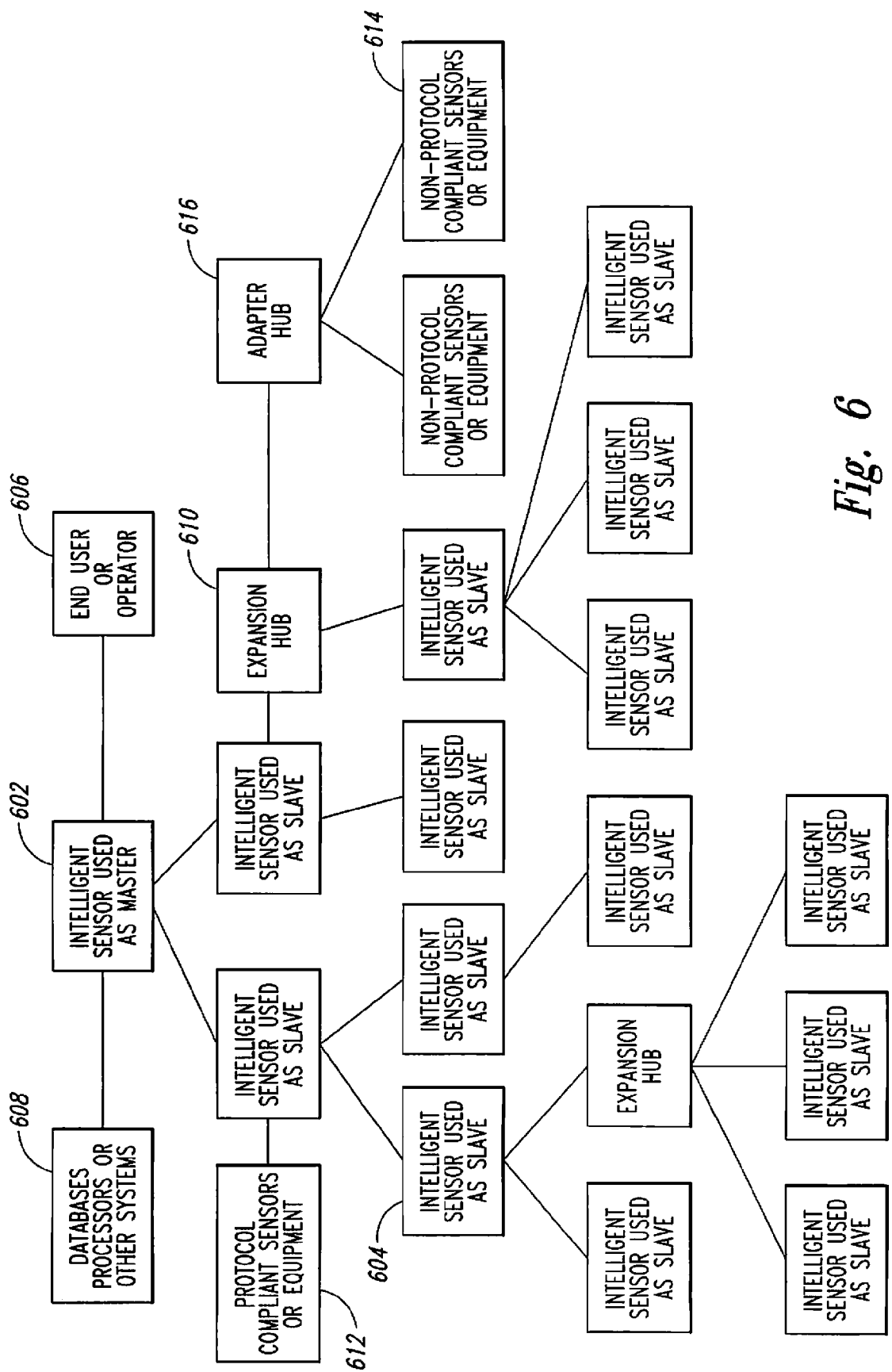
FIG. 6 is a partially schematic illustration of a master sensor and slave sensor arrangement in accordance with certain embodiments of the invention.

FIG. 6 is a partially schematic illustration of a master sensor and slave sensor arrangement in accordance with certain embodiments of the invention. In FIG. 6, an intelligent sensor system similar to the sensor system 100 discussed above is configured to operate as a master sensor assembly or master sensor system 602. Similar and/or identical intelligent sensor systems are configured to operate as slave sensor assembly or slave sensor system 604 (e.g., remotely located from the master sensor system). In the illustrated embodiment, the master sensor system is configured to communicate with the slave sensors system via connectors similar to the second connectors 170b discussed above with reference to FIG. 1, either directly between sensor systems or via an expansion hub 610. For example, in FIG. 6 a data processing device in the master sensor system and/or in the slave sensor system can include communication circuitry that allows the respective data processing devices to communicate with one another. In selected embodiments, to facilitate connectivity each sensor can include a unique identification/address.

In FIG. 6, the master sensor system is also configured to communicate with other databases, processors, and/or systems 608 via a communication device and a connector similar to the data communication device and third connectors discussed above with reference to FIG. 1. For example, in selected embodiments the master sensor system can communicate to (e.g., exchange data with) a data logging computer, a Remote Processing Unit, and/or a Central Processing Unit. In selected embodiments, at least a portion of the data supplied by the sensor system(s) can be processed remotely via a remote processing unit. In the illustrated embodiment, the master sensor system is also configured to communicate with an end user and/or an operator 606 via the communication device and the connector. For example, data can be delivered to a user in a usable format (e.g., a format displayable on the user's computer system).

Additionally, in FIG. 6 the communication device can allow an operator to interface with the master sensor system and/or other devices or components in communication with the master sensor system (e.g., slaved sensor systems). For example, in selected embodiments the operator can perform maintenance functions, perform adjustments, change settings, change sensor system configurations, and/or perform like functions via the communication device (e.g., via a computer terminal or other computing system). Additionally, the master sensor system can be configured to communicate with other devices/equipment having similar communication protocols 612 or non-protocol compliant devices or equipment 614 via adaptor hubs 616 configured to act as an interface between the respective protocols. In still other embodiments, each sensor system can be attached to an existing signal/data bus with other devices.

From the foregoing, it will be appreciated that specific embodiments of the invention have been described herein for purposes of illustration, but that various modifications may be made without deviating from the invention. For example, aspects of the invention described in the context of particular embodiments may be combined or eliminated in other embodiments. Although advantages associated with certain embodiments of the invention have been described in the context of those embodiments, other embodiments may also exhibit such advantages. Additionally, not all embodiments need necessarily exhibit such advantages to fall within the scope of the invention. Accordingly, the invention is not limited except as by the appended claims.

We claim:

1. A surface sensor system for sensing conditions on a surface and configurable to provide data to a remote location, comprising:
    an electrically insulative body having a surface portion positionable substantially coplanar with the surface;
    a data processing system within the body;
    a first sensor assembly coupled to the data processing system and having a first temperature sensor and a conductivity sensor unit within the body and coupled to the surface portion, the conductivity sensor unit having a plurality of sensing electrodes coupled to the surface portion and electrically isolated from each other by a plurality of non-conductive layers interleaved between the sensing electrodes, the conductivity sensor unit configured to detect if the surface portion is wet, partially wet, or dry; and a second sensor assembly within the body and spaced apart from the first sensor assembly, the second sensor assembly being coupled to the data processing system, the second sensor assembly having first and second electrodes spaced apart from each other and interconnected by an electrically conductive member, at least a portion of the first and second electrodes being substantially coplanar with the surface portion, the electrically conductive member being positioned adjacent to first and second windings spaced apart from each other, and a detection device connected to the first and second windings and configured to detect and measure an electrical condition in the electrically conductive member based upon the conductivity of material on the surface portion and in contact with the first and second electrodes.

2. The system of claim 1 wherein the second sensor assembly has a thermal adjustment device coupled to the first and second electrodes and configured to heat or cool at least a portion of the material on the surface portion adjacent to the first and second electrodes.

3. The system of claim 1, further comprising a communication device coupled to the data processing system and configured to send or receive data from the data processing system related to the surface conditions on the surface portion.

4. The system of claim 1, further comprising a temperature sensor operatively coupled to the data processing system and positionable remotely from the body.

5. The system of claim 1 wherein the data processing system and the first and second sensors are substantially encapsulated in an electrically insulative material forming the body.

6. The system of claim 1 wherein the second sensor assembly is a passive sensor, and further comprising an active sensor that can change the temperature of the material on the surface portion adjacent to the first and second electrodes.

7. The system of claim 1 wherein the data processing system includes communication circuitry coupleable to at least one slave sensor assembly remote from the body.

8. A surface sensor system for sensing weather-related conditions on an outdoor surface, comprising:

a support structure with a surface portion positionable substantially coplanar with the outdoor surface;

a data processing system coupleable to a remote data processor;

a first sensor assembly coupled to the data processing system and having a first temperature sensor and a conductivity sensor unit, the temperature sensor being coupled to the surface portion and configured to sense the temperature at the surface portion, the conductivity sensor unit having a plurality of sensing electrodes coupled to the surface portion and electrically isolated from each other by a plurality of non-conductive layers interleaved between the sensing electrodes, and controller that controls a sequence and timing of electrical stimulation of each of the sensing electrodes to detect an electrical resistance of material on the surface portion and in electrical contact with the electrodes; and a second sensor assembly coupled to the data processing system and to the support structure and spaced apart from the first sensor assembly, the second sensor assembly having a temperature sensor, and first and second electrodes spaced apart from each other and interconnected by an electrically conductive member, at least a portion of the first and second electrodes being substantially coplanar with the surface portion, the electrically conductive member being positioned adjacent to first and second windings spaced apart from each other, and a detection device connected to the first and second windings and electrically isolated from the electrically conductive member, the detection device being configured to detect and measure an electrical condition in the electrically conductive member based upon the conductivity of material on the surface portion and in contact with the first and second electrodes, and wherein the first and second electrodes are operatively coupled to a thermal adjustment device configured to heat or cool at least a portion of the material on the surface portion adjacent to the first and second electrodes, wherein the detection device is configured to detect a change in conductivity of the portion of the material on the surface portion adjacent to the first and second electrodes that was heated or cooled, wherein data from the temperature sensor and the first and second electrodes is provided to the data processing system for determining weather-related conditions of the material on the outdoor surface.

* * * * *